United States Patent [19]

Franz et al.

[11] Patent Number: 4,925,940
[45] Date of Patent: May 15, 1990

[54] PREPARATION OF CYCLIC N,N'-DIMETHYLUREAS

[75] Inventors: Lothar Franz, Ludwigshafen; Manfred Eggersdorfer, Frankenthal; Dieter Voges, Mannheim, all of Fed. Rep. of Germany

[73] Assignee: BASF Aktiengesellschaft, Ludwigshafen, Fed. Rep. of Germany

[21] Appl. No.: 293,358

[22] Filed: Jan. 4, 1989

[30] Foreign Application Priority Data

Jan. 5, 1988 [DE] Fed. Rep. of Germany ....... 3800083

[51] Int. Cl.$^5$ .................. C07D 239/36; C07D 233/34
[52] U.S. Cl. ..................................... 544/315; 548/317
[58] Field of Search ......................... 544/315; 548/317

[56] References Cited

U.S. PATENT DOCUMENTS 4,617,400 10/1986 Ito et al. ............................... 548/317
4,642,351 2/1987 Woo et al. ........................... 548/317

FOREIGN PATENT DOCUMENTS 1517820 7/1978 United Kingdom .

OTHER PUBLICATIONS

Liebigs Ann. Chem. Synthese und Eigenschaften . . . , 726, 89–99 (1969) H. Peterson.

*Primary Examiner*—John M. Ford
*Attorney, Agent, or Firm*—Keil & Weinkauf

[57] ABSTRACT

Cyclic N,N'-dimethylureas are prepared by catalytic hydrogenation of a cyclic urea which carries hydroxyl groups in the α-position to the two nitrogen atoms.

4 Claims, No Drawings

PREPARATION OF CYCLIC N,N'-DIMETHYLUREAS

The present invention relates to the preparation of cyclic N,N'-dimethylureas by catalytic hydrogenation of a cyclic urea which carries hydroxyl groups in the γ-position to the two nitrogen atoms.

It is known, for example from British Patent No. 1,517,820 or U.S. Pat. No. 4,617,400, that cyclic N,N'-dimethylureas can be prepared by catalytic hydrogenation of the corresponding N,N'-dimethylolureas using a palladium/active carbon hydrogenation catalyst.

However, the known processes are unsatisfactory, since the hydrogenation requires the nobel metal to be used in a large amount, based on the N,N'-dimethylolureas to be hydrogenated. Furthermore, because active carbon is used as the carrier, regeneration of the spend catalysts by the methods usually employed, for example by burning off deposits, is not possible.

There was therefore a need for a process for the preparation of cyclic N,N'-dimethylureas, in which the disadvantages of the known processes can be avoided.

We have found an advantageous process for the preparation of cyclic N,N'-dimethylureas of the general formula (I)

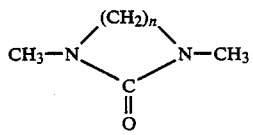

where n is 2 or 3, by hydrogenating a cyclic urea of the general formula (II)

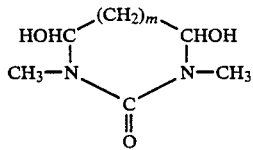

where m is 0 or 1, or of the general formula (III)

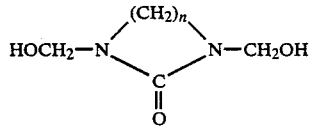

where n is 2 or 3, in the presence of hydrogen and of a hydrogenation catalyst, wherein the hydrogenation catalyst used is palladium on an inorganic carrier, and the supported catalyst additionally contains sulfur, selenium and/or tellurium.

In the novel process, it is possible to obtain good yields of the cyclic N,N'-dimethylureas, even with the use of relatively small amounts of hydrogenation catalysts and accordingly a small amount, based on the cyclic dihydroxyureas to be hydrogenated, of the palladium component. Moreover, the catalyst can be regenerated in a simple manner, for example by combustion.

The starting materials used for the novel process are cyclic ureas of the general formula (II)

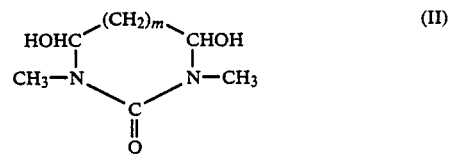

where m is 0 or 1 (cf. Liebigs Ann. Chem. 726 (1969), 8999). Other starting materials employed are cyclic ureas of the general formula (III)

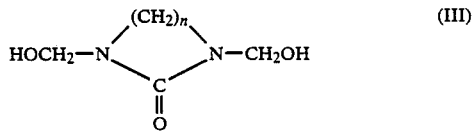

where n is 2 or 3, e.g. N,N'-dimethylolethyleneurea or N,N'-dimethylolpropyleneurea.

The cyclic ureas of the general formula (III) can be used as such. However, it is also possible first to prepare the cyclic ureas of the general formula (III) in a reaction vessel by reacting a cyclic urea of the general formula (IV)

where n is 2 or 3, with formaldehyde in the presence of hydrogen and of the novel hydrogenation catalyst and then to hydrogenate the resulting cyclic N,N'-dimethylolurea of the general formula (III), at the rate at which it is formed, to give a cyclic N,N'-dimethylurea of the general formula (I). In this procedure, the conditions, such as pressure and temperature, which are used for the hydrogenation are also applicable to the preceding reaction with formaldehyde to give the cyclic N,N'-dimethylolureas formed as intermediates.

For the preparation of the cyclic ureas of the general formula (III), formaldehyde may be used as such, for example in aqueous or methanolic solution. However, it is also possible to use substances, such as paraformaldehyde or trioxane, which release formaldehyde under the reaction conditions. The formaldehyde is generally employed in a stoichiometric amount or in excess, for example in up to twice the stoichiometric amount.

The hydrogenation catalyst used according to the invention is palladium on an inorganic carrier, the supported catalyst additionally containing sulfur, selenium and/or tellurium. The inorganic carriers used are in general carbonates, oxides, phosphates, silicates and sulfates of the elements of main groups II, III and IV of the Periodic Table. Examples of suitable carriers are alumina, silica gel, titanium dioxide and magnesium dioxide. Alumina, in particular γ-alumina, is preferably used. The palladium content of the hydrogenation catalysts is in general from 0.1 to 4, preferalby from 0.5 to 4, in particular 0.5 to 2, % by weight, based on the total supported catalyst. The content of the chalcogens sulfur, selenium and/or tellurium is advantageously from 0.1 to 5, preferably from 0.2 to 3, in particular from 0.2 to 1.5, % by weight, based on the total supported catalyst.

It may be advantageous additionally to dope the hydrogenation catalyst with rare earth metals, such as scandium, yttrium or cerium. In general, the hydrogenation catalysts contain from 0.05 to 10, preferably from 0.05 to 5, in particular from 0.1 to 5, % by weight, calculated as oxides and based on the supported catalyst, of the rare earth metals, which are generally used in the form of the oxides. The hydrogenation catalyst is advantageously used in amounts such that the weight ratio of the palladium contained in the hydrogenation catalyst to the cyclic dihydroxyureas to be hydrogenated is from 1: 10,000 to 50:1,000, preferably from 1:10,000 to 15: 1,000, in particular from 5:10,000 to 10:1,000.

The hydrogenation is advantageously carried out in a solvent. Examples of suitable solvents are water and polar organic solvents, for example alcohols, such as methanol, ethanol, propanol, isopropanol, butanol or isobutanol.

It may be advantageous to carry out the hydrogenation in the presence of a mineral acid, such as sulfuric acid or phosphoric acid, an organic sulfonic acid or an ion exchanger. Examples of suitable organic sulfonic acids are benzene fulsonic acid and p-toluenesulfonic acid. Preferred ion exchangers are ion exchangers in the hydrogen form. Examples of suitable ion exchangers are sulfonated carbons, sulfonated phenol/formaldehyde resins, sulfonated resins derived from cumarone/indene condensates, and in particulare sulfonated polystyrene resins, such as crosslinked styrene/divinylbenzene co-polymers sulfonated in the nucleus. The mineral acids, organic sulfonic acids and ion exchangers are generally used in amounts of from 0.5 to 100, preferably from 0.5 to 50, in particular from 1 to 20, % by weight, based on the cyclic dihydroxyureas to be hydrogenated.

The hydrogenation is generally carried out at from 80° to 200° C., preferably from 100° to 180° C., in particular from 110° to 160° C., and advantageously under superatmospheric pressure, in general from 20 to 300, preferably from 30 to 200, in particular from 40 to 150, bar.

The hydrogenation may be carried out batchwise, for example in an autoclave, or continuously.

The cyclic N,N'-dimethylureas obtainable according to the invention are used, for example, as solvents.

The Examples which follow illustrate the invention.

EXAMPLE 1

1,500 g of a 50% strength by weight aqueous solution of N,N'-dimethylolpropyleneurea, 100 g of 85% strength by weight phosphoric acid and 10 g of hydrogenation catalyst (1.15% by weight of PdO and 0.25% by weight of TeO$_2$, based in each case on the total hydrogenation catalyst, on $\gamma$-Al$_2$O$_3$) are placed in a 3.5 l stirred autoclave. The reaction mixture is hydrogenated for 10 hours at 120° C. and under a pressure of 80 bar, which is generated by forcing in the hydrogen for hydrogenation. The catalyst is separated off. Distillation under reduced pressure gives 3,754 g (62.4%) of N,N'-dimethylpropyleneurea.

EXAMPLE 2

1,500 g of a 50% strength by weight aqueous solution of N,N'-dimethylolpropyleneurea, 100 g of 85% strength by weight phosphoric acid and 10 g of a hydrogenation catalyst (1% by weight of Pd and 0.2% by weight of Se, based on each case on the catalyst, on $\gamma$-Al$_2$O$_3$) are placed in a 3.5 l stirred autoclave. The reaction mixture is hydrogenated for 10 hours at 120° C. and under a pressure of 80 bar, which is generated by forcing in the hydrogen for hydrogenation. The catalyst is separated off, and 421.9 g (73%) of N,N'-dimethylpropyleneurea were obtained in the subsequent distillation under reduced pressure.

EXAMPLE 3

1,500 g of a 50% strength by weight aqueous solution of N,N'-dimethylolpropyleneurea, 100 g of 85% strength by weight phosphoric acid and 10 g of a catalyst (1.15% of PdO, 0.5% of CeO$_2$ and 0.28% of SeO$_2$, based in each case on the catalyst, on $\gamma$-Al$_2$O$_3$) are placed in a 3.5 l stirred autoclave. The reaction mixture is hydrogenated for 10 hours at 120° C. and under a pressure of 80 bar, which is generated by forcing in the hydrogen for hydrogenation. The catalyst is separated off, and 350 g (58%) of N,N'-dimethylpropyleneurea are obtained in the subsequent distillation under reduced pressure.

EXAMPLE 4

1,500 g of a 50% strength by weight aqueous solution of N,N'-dimethylolpropyleneurea, 100 g of 85% strength by weight phosphoric acid and 10 g of a catalyst (1% of Pd and 1% of S, based on each case on the catalyst, on $\gamma$-Al$_2$O$_3$) are placed in a 3.5 l stirred autoclave. The reaction mixture is hydrogenated for 5 hours at 120° C. and under a pressure of 80 bar, which is generated by forcing in the hydrogen for hydrogenation. The catalyst is separated off and the filtrate is distilled under reduced pressure to give 537.5 g (90%) of N,N'-dimethylpropyleneurea.

EXAMPLE 5

Preparation of catalysts according to the invention (a) A mixture of 250 parts by weight of an 11% strength by weight palladium nitrate solution, 1,250 parts by weight of distilled water, 8.95 parts by weight of selenous acid and 140 parts by weight of nitric acid is added to 2,870 parts by weight of gamma-alumina.

The water is evaporated off at 120° C. in a drying drum, and the residue is calcined at 520° C. for 6 hours.

(b) A mixture of 45 parts by weight of an 11% strength by weight palladium nitrate solution, 1.82 parts by weight of telluric acid and 606 parts by weight of water is added to 495 parts by weight of gamma-alumina. Drying and calcination are carried out as described under (a).

We claim:

1. A process for the preparation of a cyclic N,N'-dimethylurea of the formula (I)

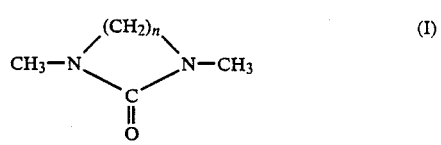

where n is 2 or 3, by hydrogenating a cyclic urea of the formula

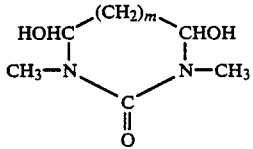

where m is 0 or 1, or of the formula (III)

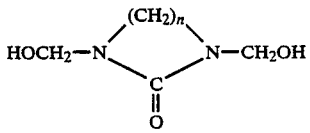

where n is 2 or 3, in the presence of hydrogen and of a hydrogenation catalyst, wherein the hydrogenation is carried out in the presence or absence of a mineral acid or an organic sulfonic acid or an acidic organic ion exchanger and in the presence of a palladium catalyst supported on an inorganic carrier selected from the carbonate, oxides, phosphates, silicates and sulfates of the elements of main groups II, III and IV of the Periodic Table, the palladium content of the catalyst ranging from 0.1 to 4% by weight, based on the total supported catalyst, the supported catalyst additionally may contain selenium and/or tellurium and/or oxides of rare earth metals, the content of the selenium and/or tellurium ranging from 0.1 to 5% by weight, based on the total supported catalyst and the content of the rare earth metal oxides, calculated as oxides and based on the total supported catalyst, ranging from 0.05 to 10% by weight.

2. A process as described in claim 1, wherein the hydrogenation is carried out in the presence of sulfuric acid, phosphoric acid, benzenesulfonic acid, p-toluenesulfonic acid, sulfonated carbons, sulfonated phenol/formaldehyde resins, sulfonated resins derived from cumarone/indene condensates or sulfonated polystyrene resins.

3. A process as described in claim 1, wherein the supported palldium hydrogenation catalyst contains the oxides of the rare earth metals scandium, yttrium or cerium.

4. A process as described in claim 1, wherein the supported palladium hydrogenation catalyst contains γ-alumina as inorganic carrier.

* * * * *